United States Patent
Reischman et al.

(10) Patent No.: US 7,241,621 B2
(45) Date of Patent: Jul. 10, 2007

(54) METHOD FOR DETERMINING RESIDUAL FUEL AND INSOLUBLES CONTAMINATION IN USED MARINE ENGINE LUBRICANTS USING UV-VISIBLE SPECTROSCOPY AND CHEMOMETRICS

(75) Inventors: Paul Thomas Reischman, Lambertville, NJ (US); Rafi Jalkian, Gibbstown, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 537 days.

(21) Appl. No.: 10/274,070

(22) Filed: Oct. 18, 2002

(65) Prior Publication Data

US 2003/0194811 A1     Oct. 16, 2003

Related U.S. Application Data

(60) Provisional application No. 60/339,994, filed on Nov. 30, 2001.

(51) Int. Cl.
   *G01N 31/00*   (2006.01)
   *G01N 21/00*   (2006.01)
(52) U.S. Cl. .................... 436/60; 436/164; 436/170
(58) Field of Classification Search .................. 436/60, 436/164, 171
   See application file for complete search history.

(56) References Cited

U.S. PATENT DOCUMENTS 5,049,738 A    9/1991 Gergely et al. ............. 250/301
5,304,807 A *  4/1994 Lin ............................ 250/373

(Continued)

FOREIGN PATENT DOCUMENTS

JP          11194124 A  *  7/1999

OTHER PUBLICATIONS

Stellam et al. "Monitoring the degradation of a synthetic lubricant oil using infrared absorption, fluorescnece emission and multivariate analysis: a fisible study", Lubrication Engineering, 1999, v. 55, No. 10, pp. 42-52.*

(Continued)

*Primary Examiner*—Yelena G. Gakh
(74) *Attorney, Agent, or Firm*—Norky L. Foss; Gary P. Katz

(57) ABSTRACT

A method for determining contamination in marine diesel lubricating oils. The method has been found to have particular utility in estimating residual fuel and insolubles contamination in marine diesel lubricating oils. The method includes the steps of: (a) obtaining spectral raw data over a frequency range substantially equivalent to that of ultraviolet-viable light for reference lubricating oil samples with known properties and concentrations of residual fuel and insolubles; (b) performing chemometric techniques to the spectral raw data obtained in step (a) to develop a calibration model and calibrate the spectral data with actual values for parameters reflecting the level of residual fuel and insolubles contamination of the reference samples, the actual values determined by means of conventional analytical methods; (c) obtaining spectra of samples of marine diesel lubricating oil of unknown concentration of residual fuel and insolubles over a frequency range substantially equivalent to that of ultraviolet-viable light; and (d) processing the obtained spectral raw data of step (c) and applying the developed calibration model to the processed data in order to determine the parameters reflecting the level of residual fuel contaminants and insolubles present in the marine diesel lubricating oil.

20 Claims, 8 Drawing Sheets

U.S. PATENT DOCUMENTS 5,672,873 A * 9/1997 Yamazoe ............... 250/339.12
5,856,870 A   1/1999 Curtiss ....................... 356/328

OTHER PUBLICATIONS

Nagase et al. JP 11194124 A, Jul. 1999, computer translation.*
Zerlia et al. "Asphaltene determination in heavy petroleum products by partial least squares analysis of UV data", Fuel 1992, v. 71, pp. 559-563.*
B. Edmonds et al. "Measurement and prediction of asphaltene precipitation from live oils", ISCOP'99, Mexico, Nov. 1999; www.infochemuk.com/publicat/aprecip8.pdf.*
Thoery of UV spectrum of UV-Vis spectroscopy, 2003, http://www.chem.ucla.edu/~bacher/General/30BL/tips/UV-VIS.html.*
Florence et al. "Applications of ATR UV/Vis spectroscopy in physical form characterization of pharmaceuticals" www.spectroscopyeurope.com, Nov. 2004.*
"ATR Probes", http://www.hellma-worldwide.de/doc_pool/en/Web_ATR_Probes.pdf.*

* cited by examiner

METHOD FOR DETERMINING RESIDUAL FUEL AND INSOLUBLES CONTAMINATION IN USED MARINE ENGINE LUBRICANTS USING UV-VISIBLE SPECTROSCOPY AND CHEMOMETRICS

CROSS REFERENCE TO RELATED APPLICATION:

Non-Provisional Application based on Provisional Application No. 60/339,994 filed Nov. 1, 2001.

FIELD OF THE INVENTION

The present invention relates to a method for determining residual fuel and insolubles contamination in used diesel engine lubricants using UV-visible spectroscopy and chemometrics.

BACKGROUND OF THE INVENTION

In recent years, diesel engines have been progressively replacing steam turbines in marine vessels, mainly as a result of the improved economics of the marine diesel. Marine diesel engines may generally be classified as slow-speed, medium-speed or high-speed engines, with the slow-speed variety being used for major, deep draft vessels. Slow-speed diesel engines are typically direct coupled, direct reversing, engines operating in the range of 90 to 250 rpm and usually run on residual fuels. These engines are of crosshead construction with a diaphragm and stuffing boxes separating the power cylinders from the crankcase to prevent combustion products from entering the crankcase and mixing with the crankcase oil. Medium-speed engines typically operate in the range of 250 to 1100 rpm and may operate on the four-stroke or two-stroke cycle. These engines are trunk piston design, and many operate on residual fuel as well. They may also operate on distillate fuel containing little or no residua. On deep-sea vessel these engines may be used for propulsion, ancillary applications or both. High-speed diesel engines are comparable to automotive trunk piston diesel engines and are normally employed in deep draft vessels only for special, ancillary applications. These engines generally require high quality distillate fuel oil for satisfactory operation.

In low-speed marine crosshead diesel engines, the cylinders and crankcase are lubricated separately, with cylinder lubrication being provided on a once-through basis by means of injection devices that apply cylinder oil to lubricators positioned around the cylinder liner. The crankcase oil provides lubrication for the bearings, gearing, valve gear and other ancillary engine components and is typically an additive-type oil selected for good oxidation and thermal stability, water demulsability, corrosion protection and good antifoam performance. Alkaline additives may also be present to neutralize any strong acids entering the crankcase through piston rod glands and detergency and extreme pressure (EP) performance may also be provided by the use of suitable additives. Similar performance characteristics are appropriate for the crankcase oils in residual fuel burning, medium-speed trunk piston engines in which the crankcase oil may also be used, in certain types, for splash cylinder lubrication. Other types of medium speed engines may have separate force feed cylinder lubrication. In either case, oil that lubricates the cylinder drains into the sump.

Two specific problems frequently arise in marine diesel engines, namely, contamination of the lubricating oil with blow-by combustion products and with residual fuel components. To a certain extent, blow-by is inevitable since some leakage around the piston rings takes place, especially with larger engine sizes. Crosshead diesel engines, in fact, generally have some blow-by products in the system oil due to the intermingling of the crankcase oil and the cylinder oil in the stuffing box. The commingled oil is generally returned to the crankcase despite the contamination. Lube oil contamination with blow-by products is more direct in medium-speed trunk piston diesel engines, where the system oil and the cylinder oil are the same. Raw residual fuel dilution may occur when seals in engine ancillaries fail to perform adequately, with the result that the chemical composition of the lubricating oil may be altered and sludge formation accelerated with possible fouling of the engine and failure of major components. Normally, a certain degree of fuel dilution is considered acceptable and in most cases up to about 5% dilution can be tolerated. Regardless the type of contamination, frequent monitoring of the engine oil is required to maintain contaminates within acceptable levels.

The formation of sludge is obviously undesirable, and it is very important to determine the cause in order to prevent damage to the engine. This is particularly so with expensive marine engines. Sludge may be formed by fuel contamination of the lubricating oil because the lubricating oil is highly paraffinic whereas the fuel oils have significant aromatic character, which may be relatively immiscible with the lubricating oil. Sludge resulting from raw fuel dilution is probably the polar, highly aromatic fraction of the fuel oil called asphaltenes. This fraction is generally only partly soluble in the lubricating oil. Also because of their aromatic character, asphaltenes have poor combustion characteristics in diesel engines.

Over the past decade, some medium-speed marine diesel engines have experienced problems with excessive deposits, with so-called "black sludge" or "black paint" increasingly found in crankcase and camshaft areas. Likewise, fuel-derived deposits have been found on piston land, ring groove and under-crown areas. Increased availability of residual fuel with declining quality, combined with higher injection pressures in modern marine engines, has led to increased fuel leakage from pumps and injectors into the lube oil sump. Unburned fuel contamination of engine lubricants has become common in these marine diesel engines.

Purifiers are known to assist greatly in cleaning sludge components from the lube oil, but the sludge still must get to the purifier before removal is possible. Unfortunately, once asphaltenes come into contact with metal components, they will often stick to them and remain. In addition, these deposits collect other oil insolubles, such as soot, by providing a sticky surface. Deposits due to asphaltenes may form in the cooler parts of the engine, such as the crank-case or camshaft areas, but they may also form on the hot piston undercrown area resulting in poor cooling of the piston crown.

Deposits and sludge formation, however, are not the only issues of concern in today's medium-speed marine diesel engines. Typically, lube oil viscosity increases and the total base number (TBN) decreases with residual fuel contamination. Oxidation and insolubles generally increase as well. These trends may also be attributed to excessive blow-by of combustion products. Therefore, detection and quantification of residual fuel contamination in used marine diesel engine oils is very important, although it is difficult to determine by conventional used oil analytical tests. Pinpointing the cause of these undesirable lube oil properties is vital for proper assessment of the maintenance action required in a particular case.

Engine builders have been, for several years, redesigning fuel equipment to minimize lube oil contamination. This, combined with the reformulation of trunk piston engine oils (TPEO's) to be more compatible with residual fuel, has resulted in cleaner engines in recent years. Still, high lube oil viscosity and low TBN remain issues today in medium-speed engines, particularly in low lube oil consumption engines. Some engine builders believe that the buildup of pentane (or heptane) insolubles, perhaps more than fuel contamination, is a primary problem. The fact that these insolubles can include asphaltenes, a residual fuel component, tends to inhibit source assessment, however.

Results of a recent study to determine the cause of viscosity increase in modern medium-speed engines indicate that residual fuel contamination is more complex than was earlier thought. Contrary to previous assumptions and observations, fuel contamination is, in at least some modern marine trunk piston diesel engines, more likely the result of unburned or partially burned asphaltenes draining off the liner into the lube oil sump or entering the sump with other blow-by combustion products. The maltenes (non-asphaltenes) fraction of the fuel is completely burned, while at least some of the asphaltenes fraction remains unburned. This study also brought attention to the importance of measuring various types of insolubles in used marine engine oil samples, including those measured by thermogravimetric analysis (TGA). Unfortunately, most methods for measuring insolubles are too time consuming and labor intensive for routine used oil analysis.

U.S. Pat. No. 5,169,785 to Altman et al. discloses a method to detect and quantify unburned residual fuel in marine engine oils based on electron spin resonance (ESR) spectroscopy. Key to the method is the fact that ESR can detect and quantify the vanadium in unburned residual fuel, which is largely present as vanadyl porphyrins. Since the vanadium byproduct from combustion, vanadium pentoxide, is not detected by ESR, any vanadium in used engine oils detected by ESR is from unburned residual fuel. In combination with conventional metals analysis, which measures total vanadium, the ESR method can determine the absolute amounts of vanadium from unburned and combusted fuel. If raw fuel, rather than partially burned fuel, is the dominant contaminant and if the vanadium content of the fuel burned in the engine is known, percent fuel dilution can be calculated. Fuel dilution accuracy is improved when the vanadium content of several recent fuel samples are averaged. This method of analysis is referred to as "Residual Fuel Detection" (RFD). The RFD test has found utility in both technical service applications and in the field-testing of new lubricant formulations. In addition, several engine builders have used it in their own engine testing and component improvement programs. While this test has been well received by industry, it is limited in the information it provides and does not measure fuel contamination directly.

As such, a need exists for a rapid, reliable method for examining residual fuel and insolubles contaminants in marine diesel lubricating oils.

SUMMARY OF THE INVENTION

The present invention relates to a method for determining contamination in marine diesel lubricating oils. The method has been found to have particular utility in rapidly estimating residual fuel and insolubles contamination in marine diesel lubricating oils and includes the steps of: (a) obtaining spectral raw data over a frequency range substantially equivalent to that of ultraviolet-visible light for reference lubricating oil samples with known properties and concentrations of residual fuel and insolubles; (b) performing chemometric techniques to the spectral raw data obtained in step (a) to develop a calibration model and calibrate the spectral data with actual values for parameters reflecting the level of residual fuel and insolubles contamination of the reference samples, the actual values determined by means of conventional analytical methods; (c) obtaining spectra of samples of marine diesel lubricating oil with unknown concentration of residual fuel and insolubles over a frequency range substantially equivalent to that of ultraviolet-visible light; and (d) processing the obtained spectral raw data of step (c) and applying the developed calibration model to the processed data in order to determine the parameters reflecting the level of residual fuel and insolubles present in the marine diesel lubricating oil. Once Steps (a) and (b) are developed, Steps (c) and (d) are quite rapid and automatable.

Accordingly, it is a primary object to provide a method for examining residual fuel contaminants in marine diesel lubricating oils.

It is another primary object to provide a method for examining insolubles contaminants in marine diesel lubricating oils.

It is a significant object to provide a method for examining contaminants in marine diesel lubricating oils that is both rapid and reliable when compared with other known methods.

These and other objects and features of the present invention will be apparent from the detailed description taken with reference to accompanying figures.

DETAILED DESCRIPTION OF THE INVENTION

Figure 1:
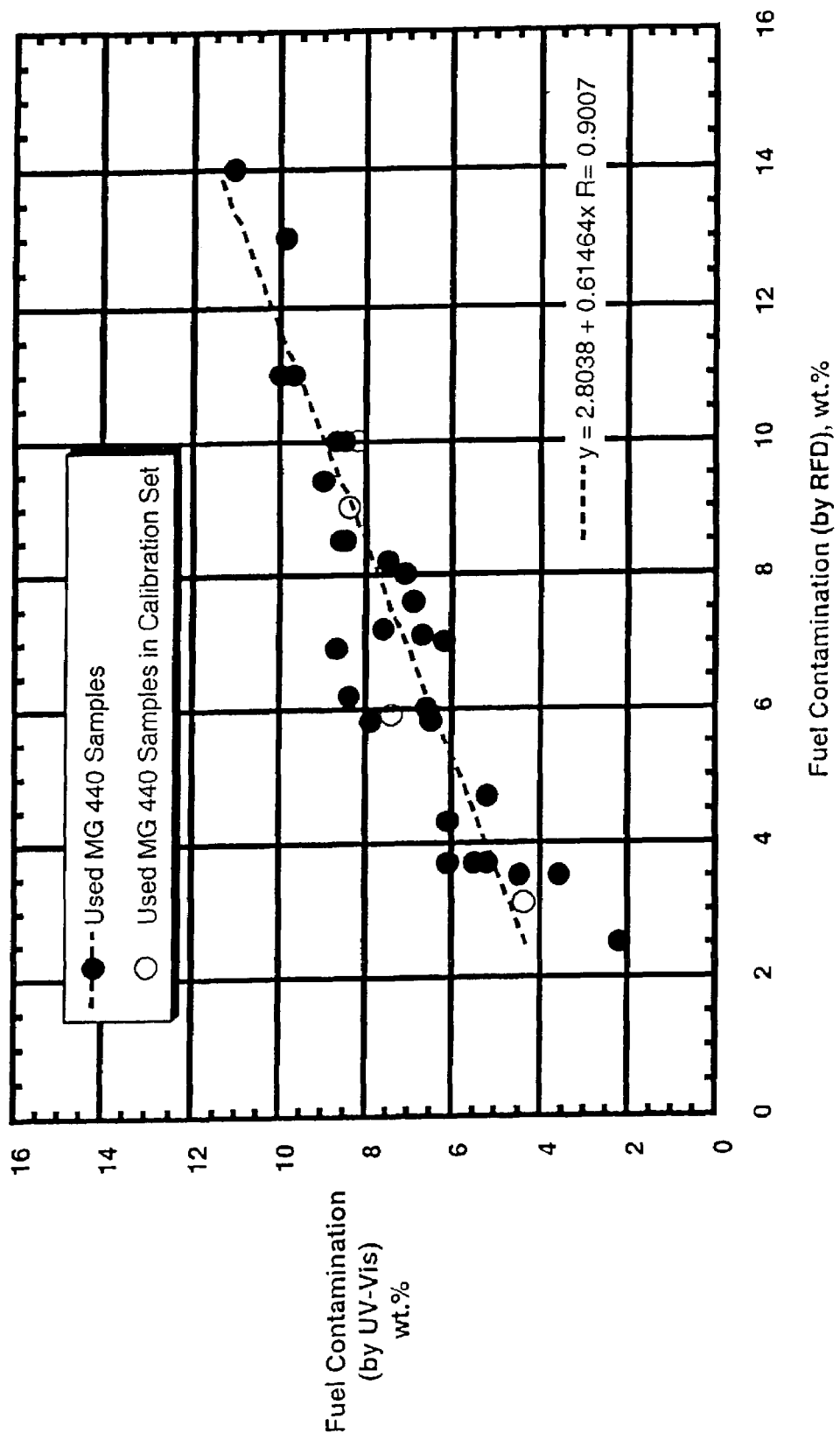
FIG. 1 shows the correlation of results obtained from the ultraviolet-visible spectroscopy method of the present invention to the Residual Fuel Detection (RFD) method of U.S. Pat. No. 5,169,785.

The content of unburned residual fuel and insolubles in used marine oils is estimated according to the present invention by ultraviolet-visible (UV-Vis) spectroscopy and chemometrics. When seeking to estimate residual fuel contaminants, a portion of the UV spectrum that is sensitive to aromatics is monitored, since the core of asphaltenes is rich with aromatic rings. The result is given as percent fuel contaminants or its equivalent based on the aromatic fuel components measured. It is important to note that knowledge of fuel characteristics is not necessary.

The UV-Vis method of the present invention may also be used to estimate various types of insolubles, which are very important to engine builders in their diagnostic efforts. One chemometric model was developed for each insolubles type. The types include pentane insolubles, toluene insolubles, Soot Index and TGA soot. This new method estimates with reasonable accuracy all of these used oil properties from a single UV-Visible spectrum, which requires only a few minutes to acquire. This is in contrast to the time and labor-intensive ASTM test methods to which some of these correlate.

The UV-Vis method of the present invention has been found to complement the RFD method of U.S. Pat. No. 5,169,785, described above, when seeking to estimate residual fuel contamination in used marine lubricating oil samples. U.S. Pat. No. 5,169,785 is hereby incorporated by reference for all that it discloses. Whereas the RFD method measures the quantity of vanadium in the form of vanadyl porphyrins, UV-Vis spectroscopy detects the aromatic character of the oil sample. From this information, the weight percent of unburned residual fuel contaminants is estimated. In essence, the two methods use two different "markers" of residual fuel. While both methods can be automated, a key advantage of the UV-Vis method is that it measures the amount of undesirable unburned fuel contaminants directly. A second advantage is that it can also estimate insolubles (pentane and/or heptane), without doing a time-consuming extraction, as well as estimate soot levels.

This UV-Visible analysis is performed by first making a dilute solution of oil (about 400 PPM) in cyclohexane. The solution is then introduced to a 1 cm flow cell. The UV-Visible spectrum is then acquired in the range of 250 to 450 nm employing a low-stray light double-monochromator spectrometer. The spectrum is corrected for path length and dilution where the final unit for the spectrum is $\mu m^{-1}$.

Spectra are acquired on a number of different samples for which key used oil properties, such as pentane insolubles, have been measured. A chemometric model is developed from this data by correlating the key properties to the spectral data. The goal of the model is to accurately estimate key properties of the oil. The set of samples used for the development of the chemometric model is called the calibration set.

For this invention, chemometric models were developed for several key used oil properties: residual fuel contamination, pentane insolubles, toluene insolubles, and soot as measured by Fourier Transform Infrared (FTIR) and by Thermogravimetric Analysis (TGA). These properties assist in pinpointing the type of contamination in the oil, particularly those related to residual fuel. A key advantage of the present invention is that all of these properties can be estimated with a single spectrum, which requires only 10 to 15 minutes to complete. It is known that the measurement of insolubles and TGA soot by conventional means typically requires an hour or more to complete, with the estimation of fuel contamination even more difficult.

Pentane Insolubles

Pentane insolubles in used marine engine oil samples include a variety of organic and inorganic matter. The organic matter can include soot, oxidized oil and asphaltenes. The inorganic matter may be dirt, sand, wear metals, calcium salts, etc. Note that heptane insolubles in used engine oils are sometimes measured, but it is not a widespread practice. These insolubles contain the same types of matter as pentane insolubles but lesser amounts of asphaltenes, and perhaps oxidized oil, are precipitated. Therefore, the total amount of heptane insolubles should never be greater than pentane insolubles.

The measurement of pentane insolubles may be conducted in a variety of ways. Two standard methods are ASTM D-893 and D-4055. ASTM D-893 is a centrifugal method and the preferred option of this method includes addition of a coagulant to help precipitate small insoluble particulates. D-4055 is a filtration method through a specified opening, such as 1.2 $\mu m$. Of these methods, engine builders typically prefer D-893 in their used oil specifications, although some use their own method.

Toluene Insolubles

Toluene insolubles in used marine oil samples include soot and a variety of inorganic matter. The inorganic matter may be dirt, sand, wear metals, calcium salts, etc. Oxidized oil and asphaltenes are soluble in toluene.

The measurement of toluene insolubles may be conducted in a variety of ways. One standard method is ASTM D-893. Again, D-893 is a centrifugal method and the preferred option of this method includes addition of a coagulant to help precipitate small insoluble particulates.

Soot Index

Soot in used marine engine oils may be measured in several ways. None, however, measure soot particles exclusively. Some laboratories use an FTIR method (DIN 51452) to measure the amount by scatter of infrared radiation relative to new oil. Net "absorbance" is measured at frequencies where there is little or no interference from the oil or additives. Soot Index is a modification of DIN 51452 whereby the net "absorbance" is measured at 3980 $cm^{-1}$ (2.51 $\mu m$) only. This gives a result similar to the TGA Soot Test (see below) up to about 3 wt %, provided there are only negligible levels of suspended inorganics large enough to scatter infrared radiation. Asphaltenes do not interfere with this test.

TGA Soot

The TGA Soot Test (ASTM D5967-Appendix 4) is a measure of remaining combustible material that does not pyrolize under nitrogen as the sample is heated to 650° C. For distillate fuel applications, this material is soot. For residual fuel applications, this material is soot plus asphaltenes (albeit vis-broken asphaltenes).

Data Analysis

Data analysis using chemometric techniques permits the development of a calibration model. There are several chemometric techniques that can be used, such as: Partial Least Squares Regression (PLS), Multilinear Regression Analysis (MLR), Principal Components Regression (PCR), Principal Component Analysis (PCA) and Discriminant Analysis. The preferred chemometric technique, in accordance with the invention is the PLS method.

Partial Least Squares Regression (PLS)

PLS is a modeling and computational method by which quantitative relations can be established between blocks of variables, e.g., a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is disclosed in detail in Carlsson R., Design and optimization in organic synthesis, B. G. M. Vandeginste, O. M. Kvalheim, Eds., Data handling in science and technology, (Elsevier, 1992), vol. 8.

Multilinear Regression Analysis (MLR)

By MLR, the best fitting plane for the kappa number as a function of the spectra is defined, using least squares techniques to define each boundary of the plane. This plane is then used to recognize and assign a predicted value to an unknown kappa number. This technique is generally limited to relatively 'clean' systems where there is not a significant amount of matrix interference and, in contrast to PLS, it requires more objects than variables.

Principal Components Regression (PCR)

PCR is closely related to PCA and PLS. As in PCA, each object in the descriptor block is projected onto a lower dimensional space yielding in scores and loadings. The scores are then regressed against the response block in a least squares procedure leading to a regression model that can be used to predict unknown samples. The same model statistics as in PLS and PCA can be used to validate the model.

Principal Component Analysis (PCA)

By PCA, a set of correlated variables is compressed into a smaller set of uncorrelated variables. This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models. In general, 2 to 15 principal components will account for 85% to 98% of the variance of the variables. Another embodiment includes the transformation of spectral data into principal components (with or without data processing) and thus monitoring the principal components as function of time and relating these values to parameters commonly used for process control.

For a tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

Discriminant Analysis

This is a method whereby, by use of spectral data, the known kappa number values are grouped into different clusters, separated by linear decision boundaries. From its spectrum, a sample of unknown kappa number then can be matched to a cluster, and the kappa number can be assigned a value, e.g., the average value of the cluster. This is a very useful technique for quality screening, but requires a very large database to obtain statistically significant results.

The following Examples illustrate the present invention and demonstrate that the residual fuel and insolubles contamination in new and used marine lubricating oils may be rapidly quantified by the use of UV-Vis method of the present invention.

EXAMPLES

Example 1

Residual Fuel Calibration Samples

To establish a calibration set of samples, the following types were included: seven sets of new Mobilgard 440 samples contaminated with residual fuel, two sets of a fresh 40 TBN competitive oil (Comp. Oil A) contaminated with residual fuel, three new engine oil samples (Mobilgard 430, Mobilgard 440 and Comp. Oil A) and eight used oil samples.

The seven sets of fuel-contaminated samples were formed by blending one of seven residual fuels with new Mobilgard 440 at approximately 2.5 wt %, 5.0 wt %, 7.5 wt % and 10 wt % levels. The seven fuels selected were obtained from various regions of the world and have a wide range of asphaltenes content. A listing of the fuel properties is in Table 1, below.

TABLE 1

Properties of Fuel Oils Used in Calibration Set

| Sample No. | Kinematic Viscosity @ 50° C. cSt | Density @ 15° C. cSt | CCAI | Sulfur wt % | Asphaltenes wt % | Vanadium (ppm) |
|---|---|---|---|---|---|---|
| 1 | 173.5 | 0.9530 | 823 | 2.6 | 7.8 | 120 |
| 2 | N/A | N/A | N/A | 1.9 | 7.9 | 100 |
| 3 | 756.7 | 0.9974 | 852 | 4.3 | 12.4 | 120 |
| 4 | 423.6 | N/A | N/A | 2.5 | 10.4 | 330 |
| 5 | 635.9 | 0.9672 | 823 | 1.9 | 9.2 | 220 |
| 6 | 15.78 | 0.9286 | 835 | 1.9 | 2.6 | 29 |
| 7 | 350.5 | 0.9860 | 848 | 2.4 | 9.1 | 81 |

Each contaminated blend was decanted and centrifuged to remove any sludge that may have formed. The amount of contamination for each sample was based on the resulting vanadium level in the oil as a percentage of the vanadium content of the fuel added.

Two of the seven test fuels were also blended with new Comp. Oil A to test the effect of additive variations. Comp. Oil A is known to have a distinctly different formulation from Mobilgard 440. Blends were made as described above and the samples included in the calibration set of samples. Additionally, three new oil samples (Mobilgard 430, Mobilgard 440, denoted in the Tables as MG 430 and MG 440, respectively, and Comp. Oil A) were included in the calibration set to test for no contamination. Eight used oil samples were selected to represent high, moderate and low fuel contamination, as determined by RFD. The amount of fuel varied from 0 to 15 wt %. A sample with zero fuel contamination, see Sample No. (98–18397), below, contained a large amount of soot. Using these samples, several chemometric models were developed to estimate fuel contamination.

The UV-Vis analysis is performed by first making a cyclohexane solution of the oil. The solution is prepared by adding a drop of oil in a disposable glass bottle and adding about 100 ml of cyclohexane to the bottle (1 drop of oil (about 0.03 g) in about 78 g solution or around 400 PPM), recording the weights of sample and solution. The solution is introduced to a 1 cm flow cell. The UV spectrum is then acquired in the range of 250 to 450 nm employing a low stray light double-monochromator spectrometer (e.g., Perkin Elmer Lambda 9, 18, or 19). The spectrum is corrected for path length and dilution where the final unit for the spectrum is $\mu m^-$. The flow cell is finally washed with cyclohexane and dried. This procedure is followed for both model development as well as unknown analysis. Results for each of the calibration samples are shown in Table 2.

TABLE 2

| Sample Number | Fuel Content (V or RFD) wt % | Fuel Content (UV-Vis) wt % | Sample Description |
|---|---|---|---|
| 8 | 2.1 | 2.3 | New MG 440 + Fuel Samp. No. 1 |
| 9 | 4.2 | 4.0 | New MG 440 + Fuel Samp. No. 1 |
| 10 | 6.7 | 6.2 | New MG 440 + Fuel Samp. No. 1 |
| 11 | 8.3 | 8.6 | New MG 440 + Fuel Samp. No. 1 |
| 12 | 2.5 | 2.9 | New MG 440 + Fuel Samp. No. 2 |
| 13 | 5.0 | 6.0 | New MG 440 + Fuel Samp. No. 2 |
| 14 | 7.5 | 8.7 | New MG 440 + Fuel Samp. No. 2 |
| 15 | 10.0 | 11.2 | New MG 440 + Fuel Samp. No. 2 |
| 16 | 2.1 | 2.3 | New MG 440 + Fuel Samp. No. 3 |
| 17 | 4.2 | 5.1 | New MG 440 + Fuel Samp. No. 3 |
| 18 | 5.8 | 6.4 | New MG 440 + Fuel Samp. No. 3 |
| 19 | 7.5 | 8.4 | New MG 440 + Fuel Samp. No. 3 |
| 20 | 2.3 | 2.6 | New MG 440 + Fuel Samp. No. 4 |
| 21 | 4.5 | 5.2 | New MG 440 + Fuel Samp. No. 4 |
| 22 | 4.5 | 5.3 | New MG 440 + Fuel Samp. No. 4 |
| 23 | 6.4 | 7.0 | New MG 440 + Fuel Samp. No. 4 |
| 24 | 2.5 | 2.0 | New MG 440 + Fuel Samp. No. 5 |
| 25 | 4.5 | 3.7 | New MG 440 + Fuel Samp. No. 5 |
| 26 | 6.8 | 5.4 | New MG 440 + Fuel Samp. No. 5 |
| 27 | 9.1 | 7.2 | New MG 440 + Fuel Samp. No. 5 |
| 28 | 2.4 | 2.2 | New MG 440 + Fuel Samp. No. 6 |
| 29 | 5.2 | 4.2 | New MG 440 + Fuel Samp. No. 6 |
| 30 | 6.9 | 6.1 | New MG 440 + Fuel Samp. No. 6 |
| 31 | 10.3 | 8.4 | New MG 440 + Fuel Samp. No. 6 |
| 32 | 2.5 | 2.5 | New MG 440 + Fuel Samp. No. 7 |
| 33 | 4.9 | 4.8 | New MG 440 + Fuel Samp. No. 7 |
| 34 | 7.4 | 7.2 | New MG 440 + Fuel Samp. No. 7 |
| 35 | 9.9 | 9.6 | New MG 440 + Fuel Samp. No. 7 |
| 36 | 0.0 | 1.7 | Used MG 440 ex M/V A |
| 37 | 13.0 | 12.4 | Used MG 440 ex M/V B |
| 38 | 15.0 | 13.6 | Used MG 440 ex M/V C |
| 39 | 5.0 | 7.7 | Used MG 440 ex M/V B |
| 40 | 9.0 | 8.4 | Used MG 440 ex M/V D |
| 41 | 10.0 | 8.2 | Used MG 440 ex M/V D |
| 42 | 3.1 | 4.4 | Used MG 440 ex M/V D |
| 43 | 5.9 | 7.4 | Used MG 440 ex M/V D |
| 44 | 0.0 | 0.1 | New MG 440 |
| 45 | 0.0 | 0.0 | New MG 430 |
| 46 | 0.0 | 0.4 | New Comp. Oil A |

UV-Visible Results on Calibration

Plots of the estimated versus the actual fuel contamination levels were made for the seven fuels in new Mobilgard 440, and the best straight line through the origin was fit through the data for each fuel. Linear correlations and slopes for each of the fuels are listed in Table 3, below.

TABLE 3

Linear Correlations for Fuel Oil Added to New Lube Oil

| Fuel Sample Number | Fuel in New Mobilgard 440 | | Fuel in Comp. Oil A | |
|---|---|---|---|---|
| | Line Slope | R Value Correlation | Line Slope | R Value Correlation |
| 1 | 0.99 | 0.991 | | |
| 2 | 1.14 | 0.998 | | |
| 3 | 1.13 | 0.996 | | |
| 4 | 1.13 | 0.994 | | |
| 5 | 0.80 | 0.999 | | |
| 6 | 0.84 | 0.995 | 0.90 | 0.986 |
| 7 | 0.97 | 1.000 | 1.08 | 0.999 |

Correlations were very good with R-values ranging from 0.991 to 1.000. Slopes ranged from 0.80 to 1.14. The expected slope is 1.000. The 20% variation slopes relative to the expected value is similar to the 20% error noted in the measurement of asphaltenes in various residua using partial least squares techniques (Zerlia, T. & Pinelli, G., FUEL, Vol. 71, 1992, pp. 559–563, the contents of which are hereby incorporated by reference for all that it discloses).

The UV-Vis model gave a contamination value of 0.4 wt % for all three contaminated new oils. A plot of the UV-Vis results versus the RFD results for the used oil samples showed a fairly good linear correlation through the origin with a slope of 0.960 and an R-value of 0.904. A better linear fit is found when the line is not forced through the origin (Slope=0.737, R=0.968).

Example 2

Testing the UV-Vis Method

The calibration set described above was evaluated by testing it with 29 additional used Mobilgard 440 samples. Also, the model was tested with two sets of four fuel-diluted new Mobilgard 440 samples made with hydroprocessed base stocks. None of these samples were included in the calibration set.

The used oil samples were from three vessels for which the fuel vanadium content is well known, so fuel contamination could be determined by RFD analysis with good accuracy. Samples were selected to provide a good range of raw fuel contamination levels. The correlation between the UV-Vis method results and the RFD results is reasonably good, although the best straight line fit does not go through the origin as shown in FIG. 1. The UV-Vis method overestimates fuel contamination at fuel dilution levels <7.25 wt % and underestimate the fuel dilution contamination levels >7.25 wt %. Still the correlation is reasonably good with R=0.90. While the UV-Vis method has been found to possess±20% error, measurement of residual fuel contaminates by the RFD method would be expected to have a similar error.

Figure 2:
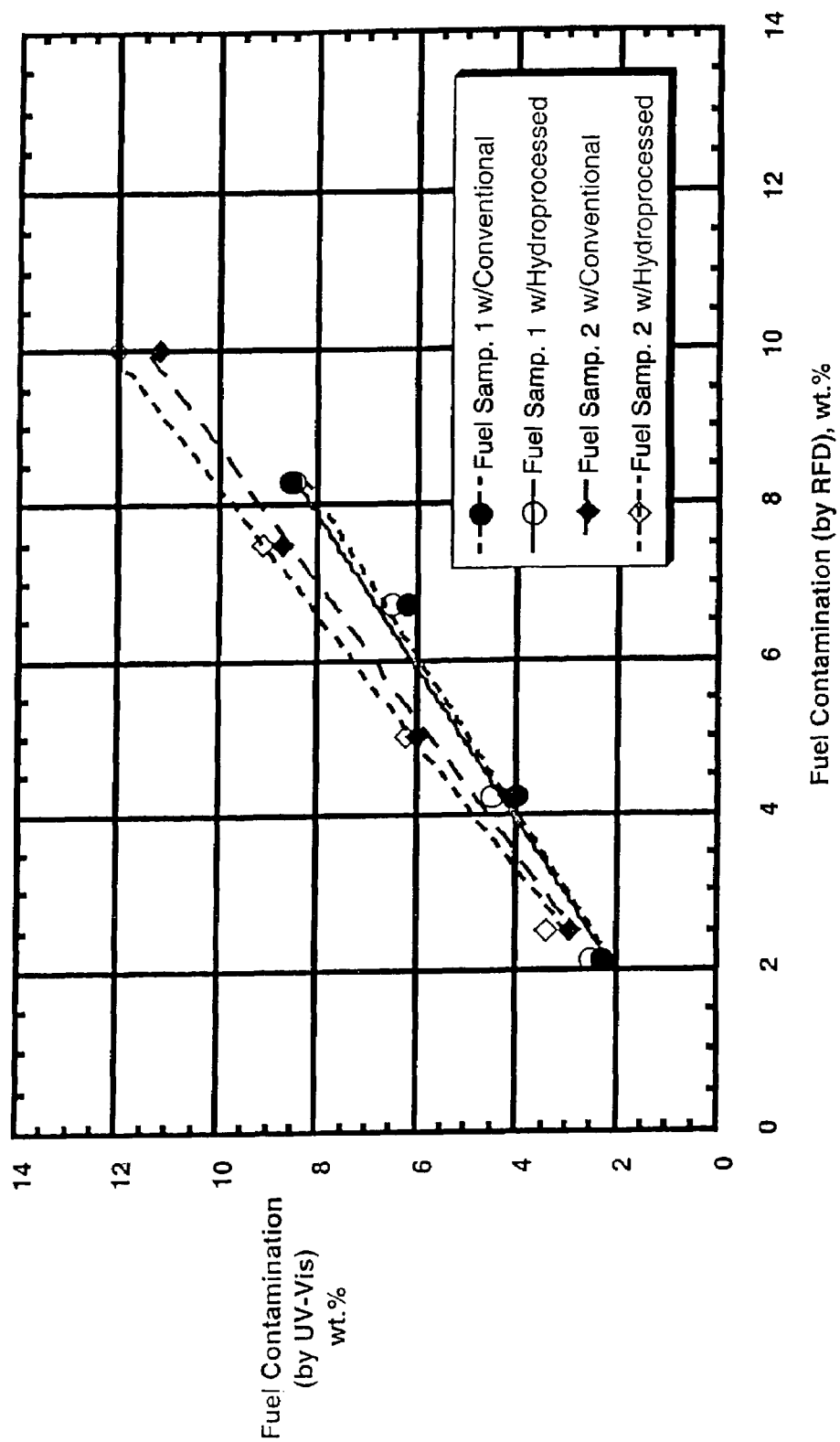
FIG. 2 shows a comparison of results obtained for conventional base stock lubricants to that obtained for hydroprocessed base stock lubricants.

The two fuel samples added to Mobilgard 440 with hydroprocessed base stock were two of the same fuels that had been added to Mobilgard 440 with conventional base stocks and included in the calibration set. Therefore, these sets can be compared to determine the effect of hydroprocessed base stock. The amount of raw fuel contamination was determined by the vanadium analysis of the contaminated oil relative to the vanadium content of the fuel added. The results showed <7% variation between the sample sets made with the same fuel (see FIG. 2). These results indicate that the UV-Vis method is not significantly affected by hydroprocessed base stocks.

Several chemometrics models were evaluated. They varied by the UV-Vis wavelength range and by the number of used oil properties included in the model. Properties included various types of insolubles test results.

Example 3

Pentane Insolubles

Figure 3:
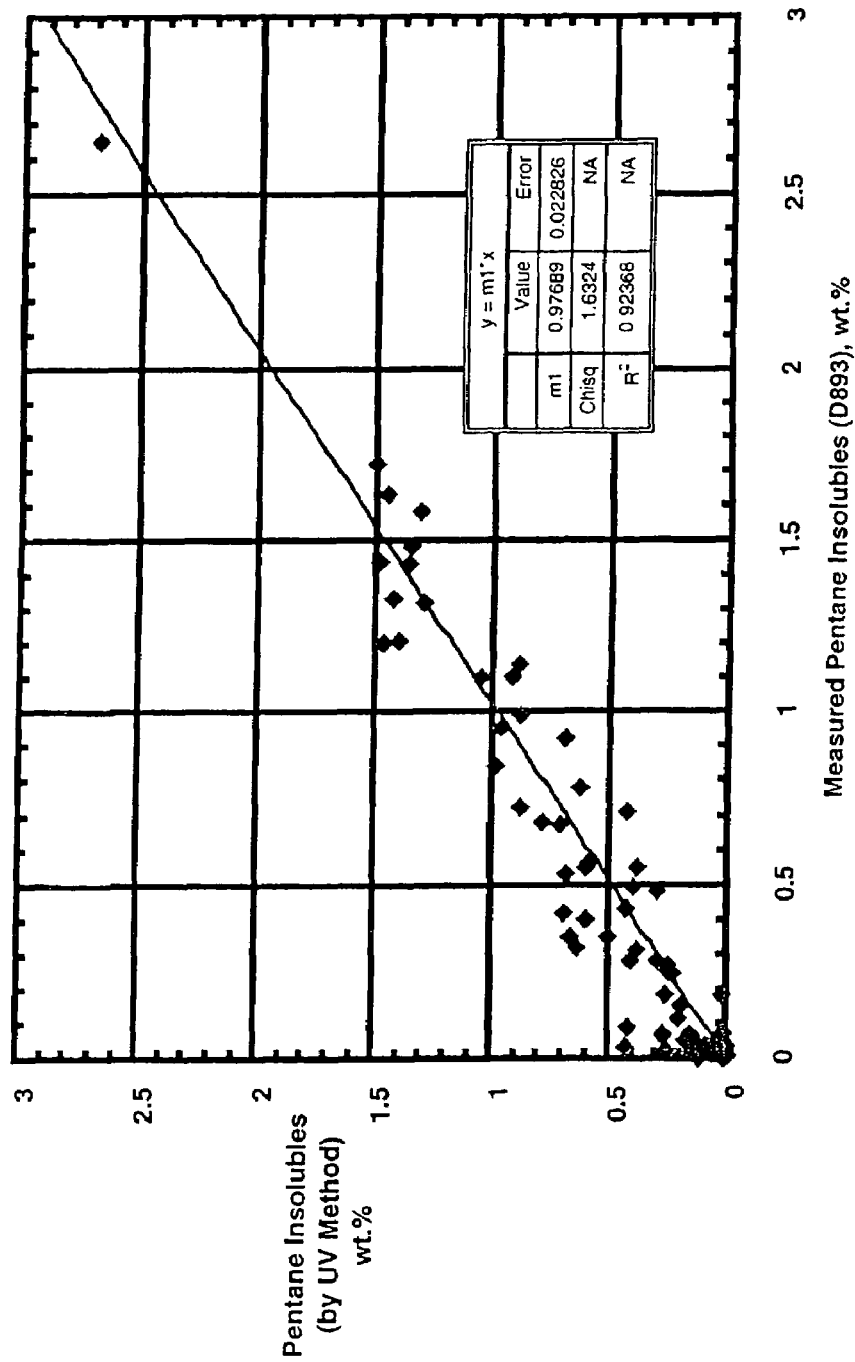
FIG. 3 shows the correlation of results obtained from the ultraviolet-visible spectroscopy method of the present invention to ASTM D-893 for pentane insolubles.

As with the establishment of the model for use in determining residual fuel contaminants, above, a chemometrics model was developed for pentane insolubles. D893 and UV-Visible estimates are shown in Table 4, below. A correlation plot of the calibration set of samples is shown in FIG. 3.

TABLE 4

UV-Visible Results

| Sample No. | Pentane Insolubles (D893b) wt % | Pentane Insolubles (UV-Vis) wt % | Sample Description |
|---|---|---|---|
| 44 |  | 0.00 | New MG 440 |
| 45 |  | 0.00 | New MG 430 |
| 8 | 0.00 | 0.00 | New MG 440 + Fuel Sample No. 1 |
| 9 | 0.00 | 0.01 | New MG 440 + Fuel Sample No. 1 |
| 10 | 0.00 | 0.11 | New MG 440 + Fuel Sample No. 1 |
| 11 | 0.27 | 0.25 | New MG 440 + Fuel Sample No. 1 |
| 12 | 0.00 | 0.00 | New MG 440 + Fuel Sample No. 2 |
| 13 | 0.00 | 0.00 | New MG 440 + Fuel Sample No. 2 |
| 14 | 0.04 | 0.09 | New MG 440 + Fuel Sample No. 2 |
| 15 | 0.15 | 0.19 | New MG 440 + Fuel Sample No. 2 |
| 16 | 0.18 | 0.02 | New MG 440 + Fuel Sample No. 3 |
| 17 | 0.48 | 0.29 | New MG 440 + Fuel Sample No. 3 |
| 18 | 0.71 | 0.43 | New MG 440 + Fuel Sample No. 3 |
| 19 | 0.78 | 0.62 | New MG 440 + Fuel Sample No. 3 |
| 20 | 0.07 | 0.01 | New MG 440 + Fuel Sample No. 4 |
| 21 | 0.24 | 0.23 | New MG 440 + Fuel Sample No. 4 |
| 22 | 0.06 | 0.27 | New MG 440 + Fuel Sample No. 4 |
| 23 | 0.09 | 0.42 | New MG 440 + Fuel Sample No. 4 |
| 24 | 0.01 | 0.00 | New MG 440 + Fuel Sample No. 5 |
| 25 | 0.03 | 0.11 | New MG 440 + Fuel Sample No. 5 |
| 26 | 0.02 | 0.26 | New MG 440 + Fuel Sample No. 5 |
| 27 | 0.03 | 0.43 | New MG 440 + Fuel Sample No. 5 |
| 47 | 0.03 | 0.00 | New Comp. Oil A + Fuel Sample 6 |
| 48 | 0.02 | 0.00 | New Comp. Oil A + Fuel Sample 6 |
| 49 | 0.07 | 0.02 | New Comp. Oil A + Fuel Sample 6 |
| 50 | 0.02 | 0.08 | New Comp. Oil A + Fuel Sample 6 |
| 51 | 0.43 | 0.43 | New Comp. Oil A + Fuel Sample 7 |
| 52 | 0.02 | 0.05 | New Comp. Oil A + Fuel Sample 7 |
| 53 | 0.07 | 0.15 | New Comp. Oil A + Fuel Sample 7 |
| 54 | 0.02 | 0.25 | New Comp. Oil A + Fuel Sample 7 |
| 28 | 0.02 | 0.00 | New MG 440 + Fuel Sample No. 6 |
| 29 | 0.02 | 0.00 | New MG 440 + Fuel Sample No. 6 |
| 30 | 0.01 | 0.00 | New MG 440 + Fuel Sample No. 6 |
| 31 | 0.00 | 0.00 | New MG 440 + Fuel Sample No. 6 |
| 32 | 0.04 | 0.00 | New MG 440 + Fuel Sample No. 7 |
| 33 | 0.03 | 0.09 | New MG 440 + Fuel Sample No. 7 |
| 34 | 0.25 | 0.25 | New MG 440 + Fuel Sample No. 7 |
| 35 | 0.49 | 0.40 | New MG 440 + Fuel Sample No. 7 |
| 55 | 0.02 | 0.06 | New MG 440 w/J500 + Fuel Samp. No. 1 |
| 56 | 0.05 | 0.17 | New MG 440 w/J500 + Fuel Samp. No. 1 |
| 57 | 0.07 | 0.27 | New MG 440 w/J500 + Fuel Samp. No. 1 |
| 58 | 0.31 | 0.38 | New MG 440 w/J500 + Fuel Samp. No. 1 |
| 59 | 0.01 | 0.06 | New MG 440 w/J500 + Fuel Samp. No. 2 |
| 60 | 0.02 | 0.14 | New MG 440 w/J500 + Fuel Samp. No. 2 |
| 61 | 0.18 | 0.26 | New MG 440 w/J500 + Fuel Samp. No. 2 |
| 62 | 0.55 | 0.38 | New MG 440 w/J500 + Fuel Samp. No. 2 |
| 36 | 2.65 | 2.69 | Used MG 430 ex M/V A |
| 37 | 1.10 | 1.05 | Used MG 440 ex M/V B |
| 38 | 1.58 | 1.31 | Used MG 440 ex M/V C |
| 39 | 0.56 | 0.59 | Used MG 440 ex M/V B |
| 63 | 0.29 | 0.48 | Used MG 440 ex M/V D |
| 64 | 0.59 | 0.60 | Used MG 440 ex M/V D |
| 65 | 0.28 | 0.41 | Used MG 440 ex M/V C |
| 66 | 0.72 | 0.88 | Used MG 440 ex M/V C |
| 67 | 0.28 | 0.29 | Used MG 440 ex M/V C |
| 68 | 0.55 | 0.60 | Used MG 440 ex M/V C |
| 69 | 0.42 | 0.69 | Used MG 440 ex M/V C |
| 70 | 0.06 | 0.14 | Used MG 440 ex M/V B |
| 71 | 0.32 | 0.63 | Used MG 440 ex M/V B |
| 72 | 0.35 | 0.66 | Used MG 440 ex M/V B |
| 73 | 0.53 | 0.68 | Used MG 440 ex M/V B |
| 74 | 1.10 | 0.92 | Used MG 440 ex M/V C |
| 75 | 0.99 | 0.88 | Used MG 440 ex M/V C |
| 76 | 1.14 | 0.89 | Used MG 440 ex M/V B |
| 77 | 0.84 | 0.98 | Used MG 440 ex M/V B |
| 78 | 0.95 | 0.96 | Used MG 440 ex M/V B |
| 79 | 1.63 | 1.45 | Used MG 440 ex M/V E |
| 80 | 1.48 | 1.35 | Used MG 440 ex M/V E |
| 81 | 1.72 | 1.50 | Used MG 440 ex M/V E |
| 82 | 0.68 | 0.78 | Used MG 440 ex M/V E |
| 83 | 1.32 | 1.29 | Used MG 440 ex M/V F |
| 84 | 1.43 | 1.36 | Used MG 440 ex PP G |
| 85 | 1.20 | 1.46 | Used MG 440 ex PP G |
| 86 | 1.33 | 1.43 | Used MG 440 ex PP G |
| 87 | 1.21 | 1.40 | Used MG 440 ex PP G |
| 88 | 1.44 | 1.48 | Used MG 440 ex PP G |
| 89 | 5.56 | 3.16 | Used MG 440 ex PP H |
| 90 | 5.68 | 3.15 | Used MG 440 ex PP H |
| 91 | 0.67 | 0.71 | Used MG 440 ex M/V I |
| 92 | 0.35 | 0.50 | Used MG 440 ex M/V I |
| 93 | 0.92 | 0.69 | Used MG 440 ex M/V I |
| 94 | 0.40 | 0.60 | Used MG 440 ex M/V I |
| 95 | 0.11 | 0.2 | Used MG 440 ex M/V I |

While the correlation plot shows some scatter particularly at low insolubles levels, a line fit through the origin has a slope near 1.0 (0.977) with an R-value of 0.92. Pentane insolubles less than 0.5 wt %, where much of the scatter is, are considered negligible. Samples with insolubles levels greater than 1.0 wt % are of most concern. Engine builder maximum limits for insolubles are generally in the 1.5 to 2.5 wt % range. The current chemometrics model makes reasonable estimates up to about 2.7 wt %.

All but four samples were included in the calibration set. The model gives reasonable estimates for all four of these samples. Although estimates for the two samples with very high insolubles (>5 wt %) show significant error, the insolubles levels are well outside the calibration set and are rarely observed that high in marine or power plant applications. Even so, estimates for these samples (>3 wt %) do indicate that the oils are unsuitable for continued use, which is sufficient information.

Example 4

Toluene Insolubles

Figure 4:
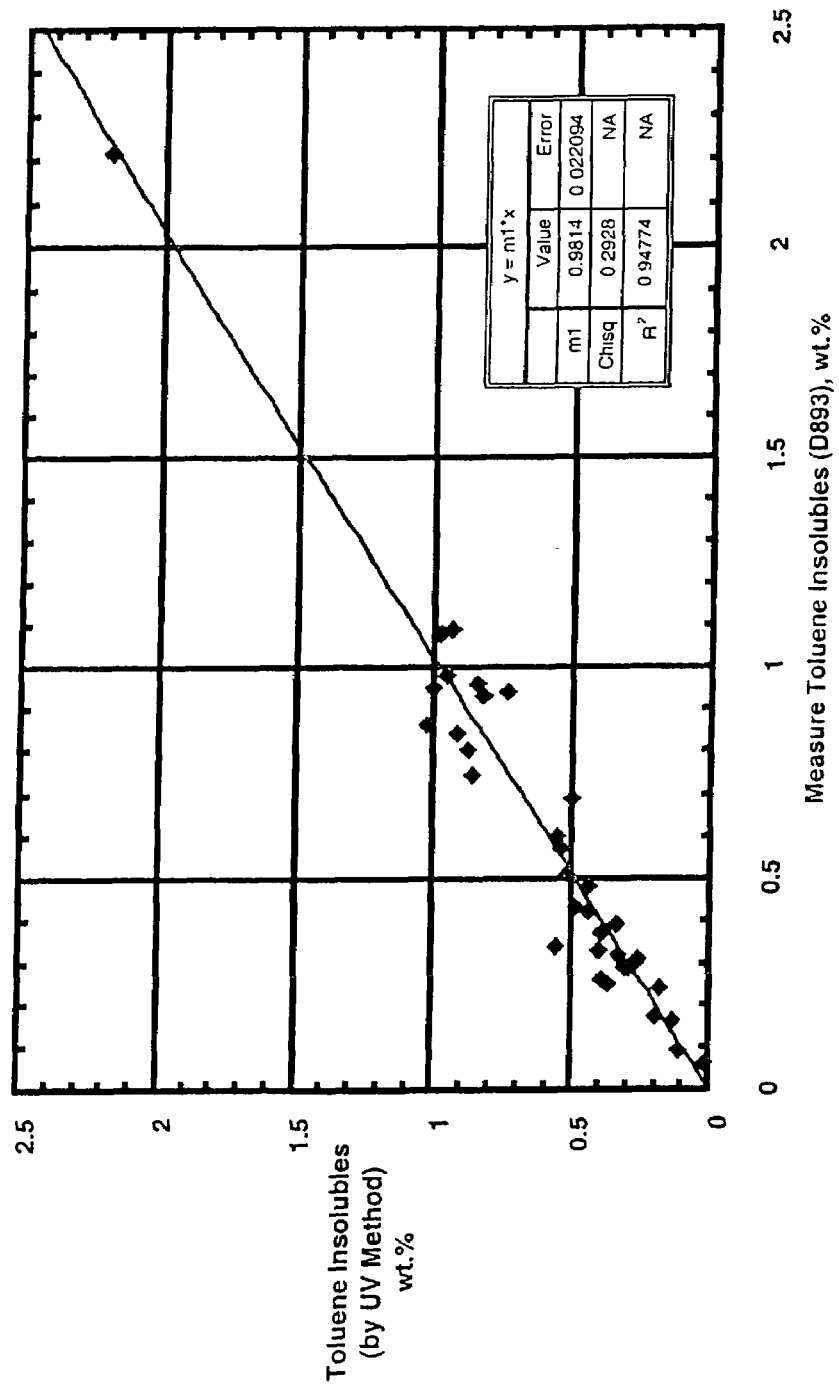
FIG. 4 shows the correlation of results obtained from the ultraviolet-visible spectroscopy method of the present invention to ASTM D-893 for toluene insolubles.

A chemometrics model was developed to estimate toluene insolubles by ASTM D893 with coagulant. The D893 and UV-Visible estimates are shown in Table 5. A correlation plot for the calibration set of samples is shown in FIG. 4.

Relative to the pentane insolubles plot in FIG. 3, the toluene insolubles plot has a little less scatter and shows a good correlation up to 2.2 wt %. A line fit through the origin has a slope near 1.0 (0.981) with an $R^2$ value of 0.95. Again, samples with insolubles levels greater than 1.0 wt % are of most concern. Engine builder maximum limits for insolubles are generally in the 1.5 to 2.5 wt % range.

As noted in Table 5, all samples were included in the calibration set except for two with high insolubles. For these samples, the model gave high but reasonable estimates thus indicating that a problem existed.

TABLE 5

UV-Visible Results

| Sample No. | Toluene Insoluble (D893b) wt % | Toluene Insoluble (UV-Vis) wt % | Sample Description |
|---|---|---|---|
| 36 | 2.21 | 2.20 | Used MG 430 ex M/V A |
| 37 | 0.94 | 0.74 | Used MG 440 ex M/V B |
| 38 | 1.09 | 0.94 | Used MG 440 ex M/V C |
| 39 | 0.30 | 0.27 | Used MG 440 ex M/V B |
| 63 | 0.24 | 0.18 | Used MG 440 ex M/V D |
| 64 | 0.37 | 0.39 | Used MG 440 ex M/V D |
| 65 | 0.17 | 0.20 | Used MG 440 ex M/V C |
| 66 | 0.51 | 0.52 | Used MG 440 ex M/V C |
| 67 | 0.16 | 0.13 | Used MG 440 ex M/V C |
| 68 | 0.29 | 0.29 | Used MG 440 ex M/V C |
| 69 | 0.26 | 0.39 | Used MG 440 ex M/V C |
| 70 | 0.06 | 0.02 | Used MG 440 ex M/V B |
| 71 | 0.29 | 0.31 | Used MG 440 ex M/V B |
| 72 | 0.32 | 0.33 | Used MG 440 ex M/V B |
| 73 | 0.39 | 0.34 | Used MG 440 ex M/V B |
| 74 | 0.42 | 0.44 | Used MG 440 ex M/V C |
| 75 | 0.43 | 0.49 | Used MG 440 ex M/V C |
| 76 | 0.57 | 0.54 | Used MG 440 ex M/V B |
| 77 | 0.34 | 0.56 | Used MG 440 ex M/V B |
| 78 | 0.60 | 0.56 | Used MG 440 ex M/V B |
| 79 | 0.95 | 1.00 | Used MG 440 ex M/V E |
| 80 | 0.96 | 0.85 | Used MG 440 ex M/V E |
| 81 | 0.86 | 1.03 | Used MG 440 ex M/V E |
| 82 | 0.48 | 0.44 | Used MG 440 ex M/V E |
| 83 | 0.98 | 0.96 | Used MG 440 ex M/V F |
| 84 | 0.93 | 0.82 | Used MG 440 ex PP G |
| 85 | 0.84 | 0.92 | Used MG 440 ex PP G |
| 86 | 0.80 | 0.88 | Used MG 440 ex PP G |
| 87 | 0.74 | 0.86 | Used MG 440 ex PP G |
| 88 | 1.08 | 0.98 | Used MG 440 ex PP G |
| 89 | 1.73 | 3.41 | Used MG 440 ex PP H |
| 90 | 2.34 | 3.43 | Used MG 440 ex PP H |
| 91 | 0.33 | 0.40 | Used MG 440 ex M/V I |
| 92 | 0.25 | 0.37 | Used MG 440 ex M/V I |
| 93 | 0.69 | 0.50 | Used MG 440 ex M/V I |
| 94 | 0.31 | 0.26 | Used MG 440 ex M/V I |
| 95 | 0.09 | 0.11 | Used MG 440 ex M/V I |

Example 4

Soot Index

Figure 5:
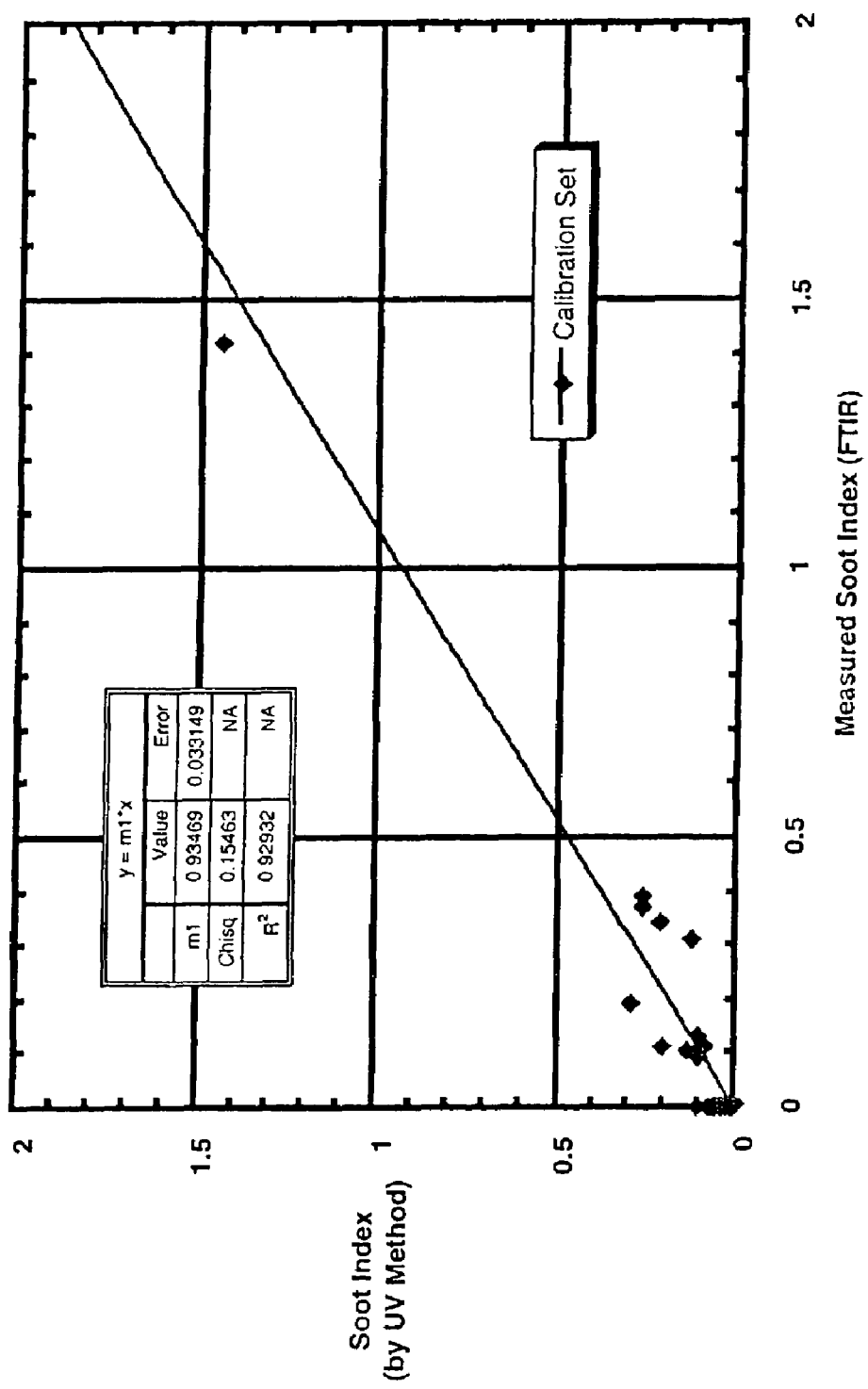
FIG. 5 shows the correlation of results obtained for the calibration set from the ultraviolet-visible spectroscopy method of the present invention to the modified Fourier transform infrared (FTIR) method DIN 51452 for Soot Index.
Figure 6:
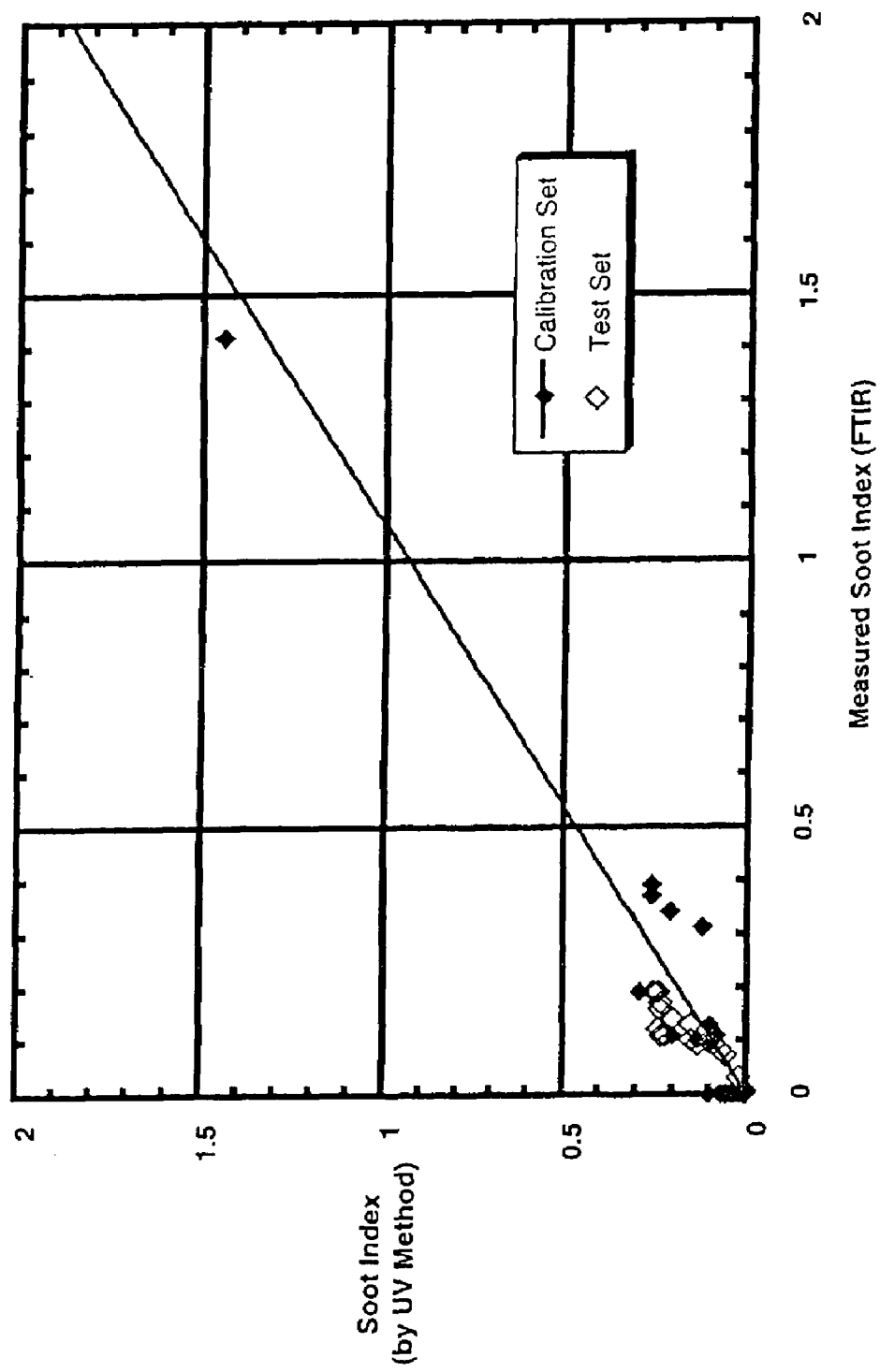
FIG. 6 shows the correlation of results obtained for both the calibration set and the test set from the ultraviolet-visible spectroscopy method of the present invention to the modified Fourier transform infrared (FTIR) method DIN 51452 for Soot Index.

A chemometrics model was developed to estimate Soot Index by modified DIN 51452 (measured at 3980 cm$^{-1}$). The Soot Index and UV-Visible estimates are shown in Table 6. Correlation plots are shown in FIGS. 5 and 6.

As shown in these Figures, the data is skewed toward low levels. That is because typical used oil samples from medium-speed diesel engines have a Soot Index <0.5. Only one sample available for this development work had a Soot Index >0.5. Still, a line fit through the origin for the calibration data has a slope near 1.0 (0.935) with an R$^2$ value of 0.93 (FIG. 5). Samples with Soot Index results >1.0 wt % are of most concern. Engine builder maximum limits for insolubles are generally in the 1.5 to 2.5 wt % range.

It should be noted that Soot Index was not actually measured on the fuel diluted new oil samples. It was assumed to be zero, which is typical for this type of sample.

Several samples, particularly used oil samples, were not included in the calibration set. FIG. 6 is a plot that includes results on all samples. The model makes reasonable estimates for the non-calibration or test samples. None of the test samples had a measured Soot Index greater than 0.5.

TABLE 6

UV-Visible Results

| Sample Number | Soot Index (DIN51 452) wt % | Soot Index (UV-Vis) wt % | Sample Description |
|---|---|---|---|
| 46 | 0.00 | 0.00 | New MG 440 |
| 47 | 0.00 | 0.00 | New MG 430 |
| 8 | 0.00 | 0.02 | New Comp. Oil A |
| 9 | 0.00 | 0.00 | New MG 440 + Fuel Samp. No. 1 |
| 10 | 0.00 | 0.00 | New MG 440 + Fuel Samp. No. 1 |
| 11 | 0.00 | 0.00 | New MG 440 + Fuel Samp. No. 1 |
| 12 | 0.00 | 0.00 | New MG 440 + Fuel Samp. No. 1 |
| 13 | 0.00 | 0.00 | New MG 440 + Fuel Samp. No. 2 |
| 14 | 0.00 | 0.01 | New MG 440 + Fuel Samp. No. 2 |
| 15 | 0.00 | 0.03 | New MG 440 + Fuel Samp. No. 2 |
| 16 | 0.00 | 0.06 | New MG 440 + Fuel Samp. No. 2 |
| 17 | 0.00 | 0.00 | New MG 440 + Fuel Samp. No. 3 |
| 18 | 0.00 | 0.04 | New MG 440 + Fuel Samp. No. 3 |
| 19 | 0.00 | 0.04 | New MG 440 + Fuel Samp. No. 3 |
| 20 | 0.00 | 0.07 | New MG 440 + Fuel Samp. No. 3 |
| 21 | 0.00 | 0.01 | New MG 440 + Fuel Samp. No. 4 |
| 22 | 0.00 | 0.05 | New MG 440 + Fuel Samp. No. 4 |
| 23 | 0.00 | 0.06 | New MG 440 + Fuel Samp. No. 4 |
| 24 | 0.00 | 0.10 | New MG 440 + Fuel Samp. No. 4 |
| 25 | 0.00 | 0.00 | New MG 440 + Fuel Samp. No. 5 |
| 25 | 0.00 | 0.04 | New MG 440 + Fuel Samp. No. 5 |
| 26 | 0.00 | 0.06 | New MG 440 + Fuel Samp. No. 5 |
| 27 | 0.00 | 0.10 | New MG 440 + Fuel Samp. No. 5 |
| 47 | 0.00 | 0.00 | New Comp. Oil A + Fuel No. 6 |
| 48 | 0.00 | 0.00 | New Comp. Oil A + Fuel No. 6 |
| 49 | 0.00 | 0.00 | New Comp. Oil A + Fuel No. 6 |
| 50 | 0.00 | 0.00 | New Comp. Oil A + Fuel No. 6 |
| 51 | 0.00 | 0.04 | New Comp. Oil A + Fuel No. 7 |
| 52 | 0.00 | 0.01 | New Comp. Oil A + Fuel No. 7 |
| 53 | 0.00 | 0.02 | New Comp. Oil A + Fuel No. 7 |
| 54 | 0.00 | 0.03 | New Comp. Oil A + Fuel No. 7 |
| 28 | 0.00 | 0.00 | New MG 440 + Fuel No. 6 |
| 29 | 0.00 | 0.00 | New MG 440 + Fuel No. 6 |
| 30 | 0.00 | 0.00 | New MG 440 + Fuel No. 6 |
| 31 | 0.00 | 0.00 | New MG 440 + Fuel No. 6 |
| 32 | 0.00 | 0.00 | New MG 440 + Fuel No. 7 |
| 33 | 0.00 | 0.00 | New MG 440 + Fuel No. 7 |
| 34 | 0.00 | 0.03 | New MG 440 + Fuel No. 7 |
| 35 | 0.00 | 0.05 | New MG 440 + Fuel No. 7 |
| 36 | 1.42 | 1.44 | Used MG 430 ex M/V A |
| 37 | 0.11 | 0.20 | Used MG 440 ex M/V B |
| 38 | 0.19 | 0.29 | Used MG 440 ex M/V C |
| 39 | 0.09 | 0.10 | Used MG 440 ex M/V B |
| 40 | 0.10 | 0.11 | Used MG 440 ex M/V D |
| 41 | 0.10 | 0.13 | Used MG 440 ex M/V D |
| 42 | 0.11 | 0.08 | Used MG 440 ex M/V D |
| 43 | 0.13 | 0.10 | Used MG 440 ex M/V D |
| 65 | 0.08 | 0.07 | Used MG 440 ex M/V C |
| 66 | 0.19 | 0.24 | Used MG 440 ex M/V C |
| 67 | 0.07 | 0.06 | Used MG 440 ex M/V C |
| 68 | 0.13 | 0.15 | Used MG 440 ex M/V C |
| 69 | 0.14 | 0.20 | Used MG 440 ex M/V C |
| 70 | 0.03 | 0.02 | Used MG 440 ex M/V B |
| 71 | 0.09 | 0.13 | Used MG 440 ex M/V B |
| 72 | 0.10 | 0.15 | Used MG 440 ex M/V B |
| 74 | 0.12 | 0.24 | Used MG 440 ex M/V C |
| 75 | 0.11 | 0.23 | Used MG 440 ex M/V C |
| 76 | 0.11 | 0.22 | Used MG 440 ex M/V B |
| 77 | 0.34 | 0.21 | Used MG 440 ex M/V B |
| 79 | 0.37 | 0.26 | Used MG 440 ex M/V E |
| 80 | 0.39 | 0.26 | Used MG 440 ex M/V E |
| 81 | 0.37 | 0.26 | Used MG 440 ex M/V E |
| 82 | 0.31 | 0.12 | Used MG 440 ex M/V E |
| 84 | 0.16 | 0.23 | Used MG 440 ex PP G |
| 85 | 0.19 | 0.25 | Used MG 440 ex PP G |
| 86 | 0.19 | 0.24 | Used MG 440 ex PP G |

TABLE 6-continued

UV-Visible Results

| Sample Number | Soot Index (DIN51 452) wt % | Soot Index (UV-Vis) wt % | Sample Description |
|---|---|---|---|
| 87 | 0.17 | 0.23 | Used MG 440 ex PP G |
| 88 | 0.19 | 0.24 | Used MG 440 ex PP G |

Example 5

TGA Soot

Figure 7:
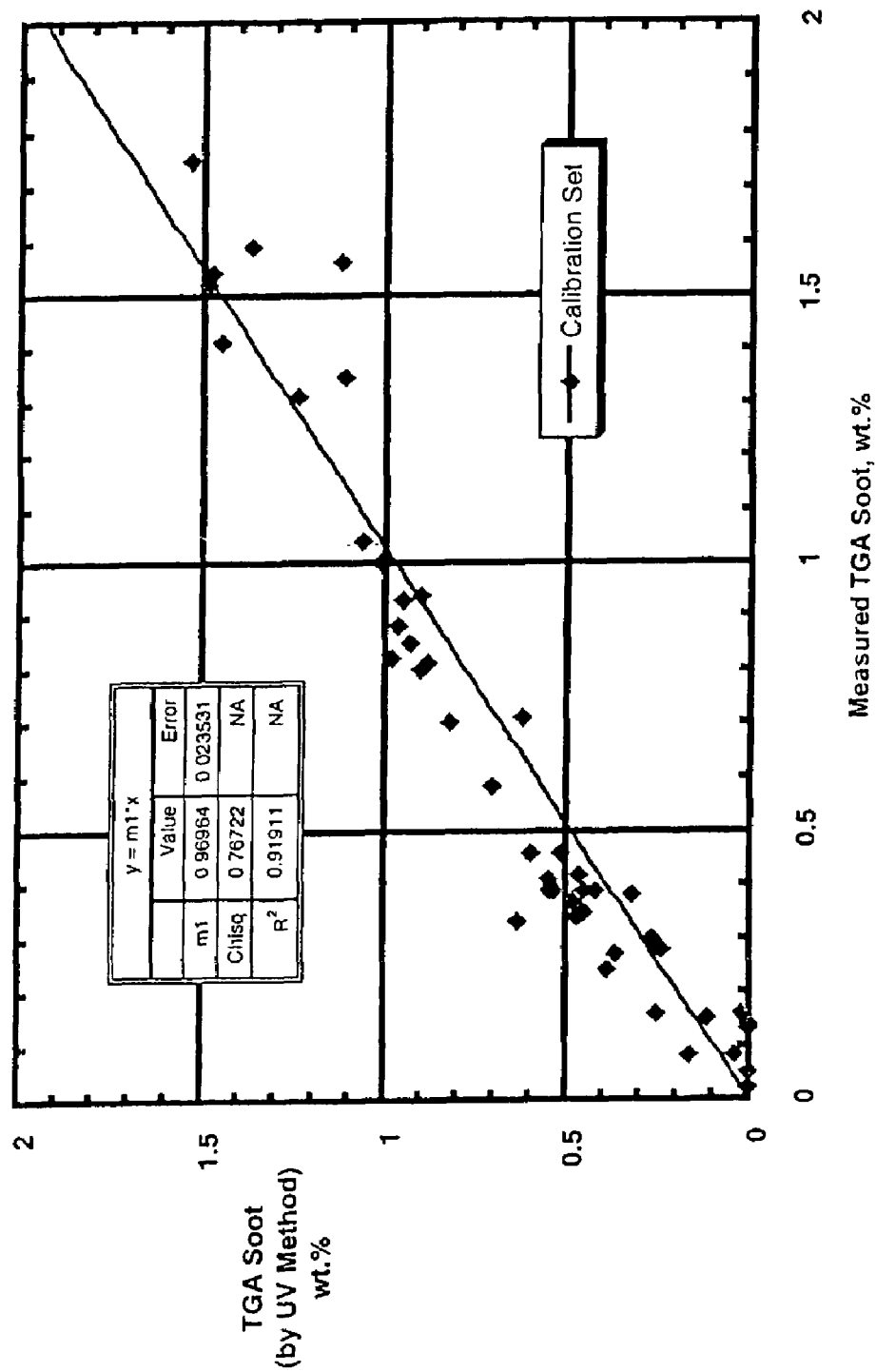
FIG. 7 shows the correlation of results obtained for the calibration set from the ultraviolet-visible spectroscopy method of the present invention to the TGA soot test, ASTM D-5967.
Figure 8:
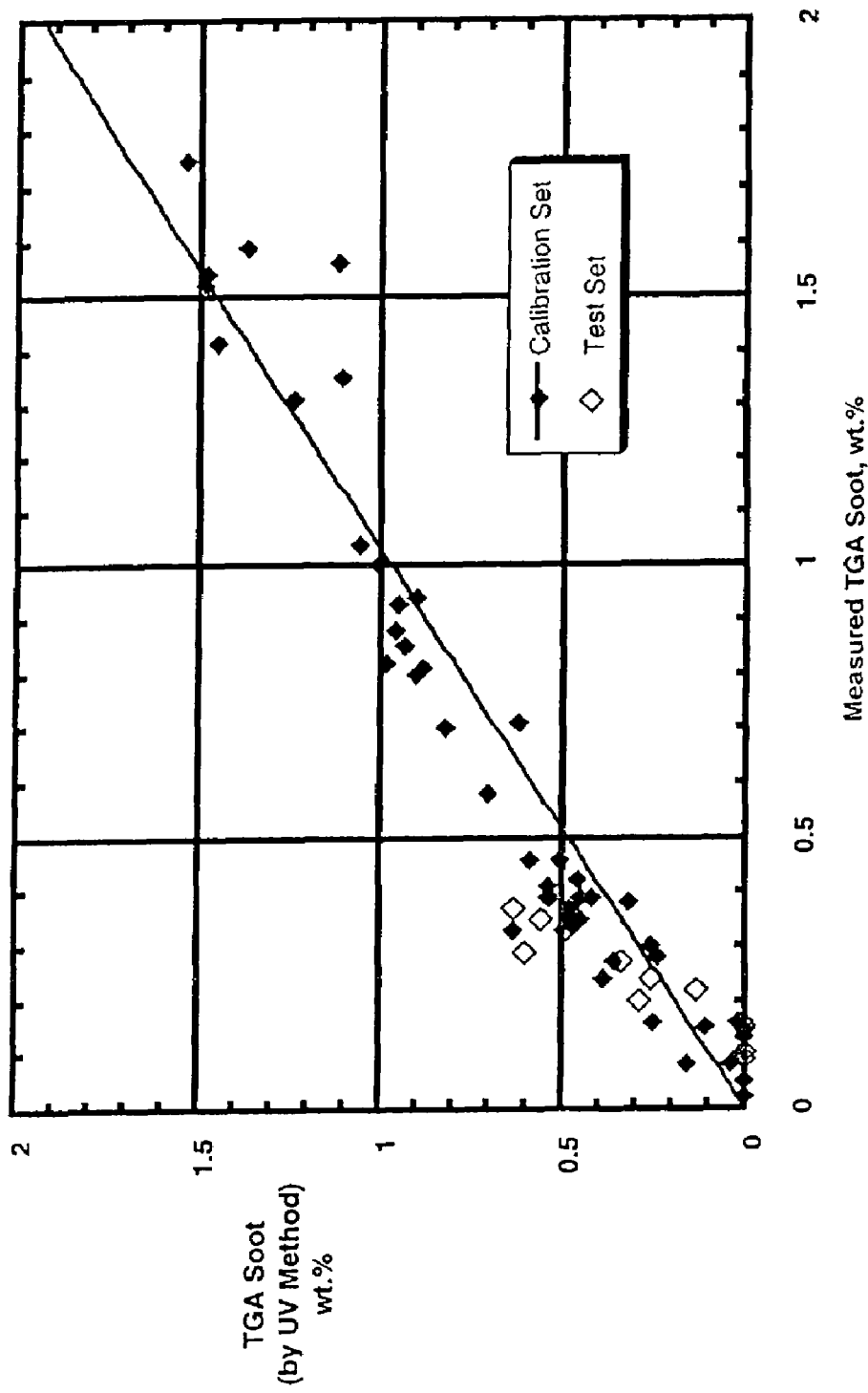
FIG. 8 shows the correlation of results obtained for both the calibration set and the test set from the ultraviolet-visible spectroscopy method of the present invention to the TGA soot test, ASTM D-5967.

A chemometics model was developed to estimate TGA soot by ASTM D5967. The TGA soot and UV-Visible estimates are shown in Table 7, below. Correlation plots of estimated versus measured TGA soot are shown in FIGS. 7 and 8.

TABLE 7

UV-Visible Results

| Sample Number | TGA Soot (D5967) wt % | TGA Soot (UV-Vis) wt % | Sample Description |
|---|---|---|---|
| 10 | 0.29 | 0.60 | New MG 440 + Fuel Sample No. 1 |
| 12 | 0.10 | 0.00 | New MG 440 + Fuel Sample No. 2 |
| 13 | 0.20 | 0.29 | New MG 440 + Fuel Sample No. 2 |
| 14 | 0.37 | 0.63 | New MG 440 + Fuel Sample No. 2 |
| 16 | 0.10 | 0.00 | New MG 440 + Fuel Sample No. 3 |
| 17 | 0.22 | 0.13 | New MG 440 + Fuel Sample No. 3 |
| 18 | 0.27 | 0.34 | New MG 440 + Fuel Sample No. 3 |
| 19 | 0.35 | 0.56 | New MG 440 + Fuel Sample No. 3 |
| 20 | 0.15 | 0.00 | New MG 440 + Fuel Sample No. 4 |
| 23 | 0.34 | 0.47 | New MG 440 + Fuel Sample No. 4 |
| 24 | 0.09 | 0.00 | New MG 440 + Fuel Sample No: 5 |
| 25 | 0.16 | 0.11 | New MG 440 + Fuel Sample No. 5 |
| 25 | 0.24 | 0.28 | New MG 440 + Fuel Sample No. 5 |
| 26 | 0.33 | 0.49 | New MG 440 + Fuel Sample No. 5 |
| 36 | 1.41 | 1.46 | Used MG 430 ex M/V A |
| 37 | 1.59 | 1.37 | Used MG 440 ex M/V B |
| 38 | 1.75 | 1.54 | Used MG 440 ex M/V C |
| 96 | 0.39 | 0.54 | Used MG 440 ex M/V D |
| 97 | 0.46 | 0.59 | Used MG 440 ex M/V D |
| 98 | 0.58 | 0.70 | Used MG 440 ex M/V D |
| 99 | 0.80 | 0.90 | Used MG 440 ex M/V D |
| 100 | 0.37 | 0.48 | Used MG 440 ex M/V D |
| 101 | 0.39 | 0.45 | Used MG 440 ex M/V D |
| 102 | 0.41 | 0.54 | Used MG 440 ex M/V D |
| 103 | 0.46 | 0.51 | Used MG 440 ex M/V D |
| 104 | 0.28 | 0.24 | Used MG 440 ex M/V D |
| 40 | 0.39 | 0.45 | Used MG 440 ex M/V D |
| 105 | 0.38 | 0.32 | Used MG 440 ex M/V D |
| 41 | 0.42 | 0.46 | Used MG 440 ex M/V D |
| 106 | 0.34 | 0.47 | Used MG 440 ex M/V D |
| 107 | 0.30 | 0.26 | Used MG 440 ex M/V D |
| 108 | 0.14 | 0.00 | Used MG 440 ex M/V D |
| 109 | 0.13 | 0.00 | Used MG 440 ex M/V D |
| 63 | 0.16 | 0.02 | Used MG 440 ex M/V D |
| 110 | 0.13 | 0.00 | Used MG 440 ex M/V D |
| 111 | 0.15 | 0.11 | Used MG 440 ex M/V D |
| 64 | 0.16 | 0.25 | Used MG 440 ex M/V D |
| 112 | 0.08 | 0.04 | Used MG 440 ex M/V D |
| 65 | 0.08 | 0.16 | Used MG 440 ex M/V C |
| 66 | 0.70 | 0.82 | Used MG 440 ex M/V C |
| 67 | 0.05 | 0.00 | Used MG 440 ex M/V C |
| 68 | 0.24 | 0.39 | Used MG 440 ex M/V C |
| 69 | 0.42 | 0.46 | Used MG 440 ex M/V C |
| 70 | 0.02 | 0.00 | Used MG 440 ex M/V B |
| 71 | 0.27 | 0.36 | Used MG 440 ex M/V B |
| 72 | 0.35 | 0.45 | Used MG 440 ex M/V B |
| 73 | 0.39 | 0.53 | Used MG 440 ex M/V B |
| 74 | 0.85 | 0.93 | Used MG 440 ex M/V C |

TABLE 7-continued

UV-Visible Results

| Sample Number | TGA Soot (D5967) wt % | TGA Soot (UV-Vis) wt % | Sample Description |
|---|---|---|---|
| 75 | 0.81 | 0.88 | Used MG 440 ex M/V C |
| 76 | 0.82 | 0.98 | Used MG 440 ex M/V B |
| 77 | 1.35 | 1.11 | Used MG 440 ex M/V B |
| 78 | 1.56 | 1.12 | Used MG 440 ex M/V B |
| 79 | 1.54 | 1.48 | Used MG 440 ex M/V E |
| 80 | 1.31 | 1.24 | Used MG 440 ex M/V E |
| 81 | 1.52 | 1.49 | Used MG 440 ex M/V E |
| 82 | 0.33 | 0.63 | Used MG 440 ex M/V E |
| 83 | 0.71 | 0.62 | Used MG 440 ex M/V F |
| 84 | 0.94 | 0.90 | Used MG 440 ex PP G |
| 85 | 1.00 | 1.01 | Used MG 440 ex PP G |
| 86 | 0.93 | 0.95 | Used MG 440 ex PP G |
| 87 | 0.88 | 0.96 | Used MG 440 ex PP G |
| 88 | 1.04 | 1.06 | Used MG 440 ex PP G |

A plot of the calibration data (FIG. 7) shows some scatter through 1.75 wt %, still a line fit through the origin has a slope near 1.0 (0.969) with an $R^2$ value of 0.92. TGA soot less than 0.5 wt % is considered negligible. Samples with insolubles levels greater than 1 wt % are of most concern. Engine builder maximum limits for insolubles are generally in the 1.5-to 2.5 wt % range.

Several samples were not included in the calibration set. FIG. 8 is a plot that includes results on all samples. The model makes reasonable estimates for the non-calibration or test samples. None of the test samples had a measured TGA soot level >0.5.

The invention may be embodied in other specific forms without departing from the spirit or essential characteristics thereof. The present description is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for determining contamination in marine diesel lubricating oils, comprising:

obtaining spectral raw data over a frequency range substantially equivalent to that of ultraviolet visible light for reference lubricating oil samples with known properties and concentrations of lubricating oil contamination;

performing chemometric techniques to the spectral raw data obtained in step (a) to develop a calibration model and calibrate the spectral data with actual values for parameters reflecting the level of contamination of the reference samples, said actual values determined by means of conventional analytical methods;

obtaining spectra of samples of marine diesel lubricating oil of unknown concentration of contaminants over a frequency range substantially equivalent to that of ultraviolet-visible light; and processing the obtained spectral raw data of step (c) and applying the developed calibration model to the processed data in order to determine the parameters reflecting the level of contaminants present in the marine diesel lubricating oil.

2. The method of claim 1, wherein the reference lubricating oil samples include both new and used lubricating oil samples.

3. The method of claim 2, wherein the lubricant oil contaminants include residual fuel.

4. The method of claim 3, wherein the lubricant oil contaminants include insolubles.

5. The method of claim 2, wherein the lubricant oil contaminants include insolubles.

6. The method of claim 5, wherein the frequency range of steps (a) and (c) is 250 to 450 nm.

7. The method of claim 2, wherein the frequency range of steps (a) and (c) is 250 to 450 nm.

8. The method of claim 3, wherein the frequency range of steps (a) and (c) is 250 to 450 nm.

9. The method of claim 4, wherein the frequency range of steps (a) and (c) is 250 to 450 nm.

10. The method of claim 1, wherein the contaminants include residual fuel and insolubles.

11. A method for determining residual fuel and insolubles contamination in marine diesel lubricating oils, comprising:

obtaining spectral raw data over a frequency range substantially equivalent to that of ultraviolet visible light for reference lubricating oil samples with known properties and concentrations of residual fuel and insolubles;

performing chemometric techniques to the spectral raw data obtained in step (a) to develop a calibration model and calibrate the spectral data with actual values for parameters reflecting the level of residual fuel and insolubles contamination, of the reference samples, said actual values determined by means of conventional analytical methods;

obtaining spectra of samples of marine diesel lubricating oil of unknown concentration of residual fuel and insolubles over a frequency range substantially equivalent to that of ultraviolet visible light; and processing the obtained spectral raw data of step (c) and applying the developed calibration model to the processed data in order to determine the parameters reflecting the level of residual fuel and insolubles present in the marine diesel lubricating oil.

12. The method of claim 11, wherein the reference lubricating oil samples include both new and used lubricating oil samples.

13. The method of claim 12, wherein the lubricant oil contaminants include residual fuel.

14. The method of claim 13, wherein the lubricant oil contaminants include insolubles.

15. The method of claim 12, wherein the lubricant oil contaminants include insolubles.

16. The method of claim 15, wherein the frequency range of steps (a) and (c) is 250 to 450 nm.

17. The method of claim 12, wherein the frequency range of steps (a) and (c) is 250 to 450 nm.

18. The method of claim 13, wherein the frequency range of steps (a) and (c) is 250 to 450 nm.

19. The method of claim 14, wherein the frequency range of steps (a) and (c) is 250 to 450 nm.

20. The method of claim 11, wherein the insolubles include pentane insolubles, toluene insolubles and soot.

* * * * *